United States Patent
Okuno et al.

(10) Patent No.: US 6,500,124 B2
(45) Date of Patent: Dec. 31, 2002

(54) ULTRASONIC DIAGNOSTIC APPARATUS AND ULTRASONIC DIAGNOSTIC METHOD CAPABLE OF ADJUSTING GAIN AND CONTRAST

(75) Inventors: Yoshiyuki Okuno, Fussa (JP); Takahiro Echizenya, Hino (JP)

(73) Assignee: Olympus Optical Co., Ltd., Tokyo (JP)

( * ) Notice: Subject to any disclaimer, the term of this patent is extended or adjusted under 35 U.S.C. 154(b) by 33 days.

(21) Appl. No.: 09/864,987

(22) Filed: May 24, 2001

(65) Prior Publication Data

US 2002/0002334 A1 Jan. 3, 2002

(30) Foreign Application Priority Data

May 25, 2000 (JP) ........................ 2000-155193

(51) Int. Cl.⁷ ................................ A61B 8/00
(52) U.S. Cl. ...................... 600/443; 600/458
(58) Field of Search .................. 600/407, 437, 600/440–447, 449, 450–459; 73/146, 622, 625, 626; 708/207; 367/7, 11, 130, 138; 424/9.51, 9.52

(56) References Cited

U.S. PATENT DOCUMENTS

| | | | |
|---|---|---|---|
| 5,029,587 A | | 7/1991 | Baba et al. |
| 5,279,301 A | * | 1/1994 | Tsukaya et al. .............. 600/442 |
| 5,313,948 A | * | 5/1994 | Murashita et al. ........... 600/443 |
| 5,433,204 A | * | 7/1995 | Olson .......................... 600/454 |
| 5,540,097 A | * | 7/1996 | Hisata .......................... 348/28 |
| 5,808,296 A | * | 9/1998 | McMonagle et al. ........ 250/221 |
| 5,860,931 A | * | 1/1999 | Chandler ..................... 600/458 |
| 5,877,819 A | * | 3/1999 | Branson ...................... 348/620 |

* cited by examiner

Primary Examiner—Marvin M. Lateef
Assistant Examiner—Ali M Imam
(74) Attorney, Agent, or Firm—Scully, Scott, Murphy & Presser

(57) ABSTRACT

A PC board of a PC has a controller for controlling a motor drive circuit based on a timing signal, a memory for GAIN/STC for storing amplification data in an data in an amplifier for GAIN/STC as digital data and outputting the stored data synchronously with the timing signal of the controller, and a PC internal bus controller for connecting a PC internal bus to a local bus. Set values of GAIN and STC are converted into parameters and are set to the memory for GAIN/STC and a set value of contrast is converted into a parameter and is set to the controller both in a live state and in a freeze state.

6 Claims, 9 Drawing Sheets

ULTRASONIC DIAGNOSTIC APPARATUS AND ULTRASONIC DIAGNOSTIC METHOD CAPABLE OF ADJUSTING GAIN AND CONTRAST

This application claims benefit of Japanese Application No. 2000-155193 filed in Japan on May 25, 2000, the contents of which are incorporated by this reference.

BACKGROUND OF THE INVENTION

1. Field of the Invention

The present invention relates to an ultrasonic diagnostic apparatus and an ultrasonic diagnostic method, and more particularly, to an ultrasonic diagnostic apparatus and an ultrasonic diagnostic method characteristic of the adjust of gain or dynamic range.

2. Related Art Statement

An ultrasonic diagnostic apparatus is put into practical use for obtaining a biogenic tomogram by irradiating an ultrasonic pulse in vivo and receiving a reflection wave from a biogenic tissue. In particular, an ultrasonic endoscope is used for diagnosing a phenomenally-undecided case by inserting the ultrasonic endoscope into the celom.

FIG. 8 is a block diagram showing the configuration of a conventional ultrasonic diagnostic apparatus of a mechanical scanning system. A motor drive circuit 102 controlled by a controller 101 drives a motor 103, thereby rotating a transducer 104. The rotation of the transducer 104 causes the controller 101 to capture a timing signal indicating a rotational position of the motor 103 which is outputted from a position detecting circuit 105 comprising an encoder, etc. Based on the timing signal, the controller 101 controls a transmission signal generator 106 and a transmitting amplifier 107, and the transducer 104 connected to the transmitting amplifier 107 emits an ultrasonic pulse.

The transducer 104 receives an echo of an invivo ultrasonic pulse, a receiving amplifier 108 and a band-pass filter (BPF) 109 remove an unnecessary signal component from the signals received by the transducer 104, and a detecting circuit 110 detects a wave. An amplifier 111 for GAIN/STC amplifies the detected received signal to a set size, the amplified signal passes through a contrast circuit 112 and a low-pass filter (LBP) 113, the signal is converted into a digital signal by an A/D converter 114 and, thereafter, it is stored in an FIFO 115.

Herein, in the amplifier 111 for GAIN/STC, the controller 101 can set the amount of amplification via a buffer 116 for GAIN/STC and a D/A converter 117.

The data stored in the FIFO 115 is coordinate transformed by an address controller 118 and a look-up table (LUT) 119 for coordinate transformation and is stored in a predetermined position of a memory 120. Here, a CPU 121 controls the controller 101 and the address controller 118.

The controller 101 performs the above-mentioned operation at intervals with a predetermined period till one rotation of the transducer 104. Received data corresponding to the one rotation is stored in the memory 120, is thereafter subjected to interpolation by an LUT 123 for interpolation in an interpolating circuit 122, passes through a video processing circuit 124, and is displayed on a monitor 125.

The controller 101 executes various control operation based on a set value of data which is transmitted from an operation setting unit 126 comprising a key board, etc.

FIG. 9 shows the configuration in the case in which gain and contrast of the received signal in FIG. 8 are adjusted after the digital conversion. The motor drive circuit 102 controlled by the controller 101 drives the motor 103, thereby rotating the transducer 104. The controller 101 captures the timing signal indicating the rotational position of the motor 103 outputted from the position detecting circuit 105. The controller 101 controls the transmission signal generator 106 and the transmitting amplifier 107 based on the timing signal, and the transducer 104 connected to the transmitting amplifier 107 emits the ultrasonic pulse.

The transducer 104 receives the echo of the invivo ultrasonic pulse, the receiving amplifier 108 and the band-pass filter (BPF) 109 remove an unnecessary signal component from the signals received by the transducer 104, and the detecting circuit 110 detects a wave. The above-described operation is similar to that of FIG. 8.

An A/D converting circuit 131 converts the detected received signal into a digital signal and the converted signal is stored in a memory 132 for pre-process. The controller 101 allows a ROM 133 for STC to output the received data converted into the digital signal by the memory 132 for pre-process. The ROM 133 for STC sets the received data from the memory 132 for pre-process and the set value from the controller 101 to an address, and outputs data in the ROM 133 for STC at a designated address to a ROM 134 for GAIN/contrast.

Data in the ROM 133 for STC is read by changing the set value from the controller 101 synchronously with the reading of the data. Thereby, gain in a distance direction changes.

Further, the ROM 134 for GAIN/contrast sets data outputted from the ROM 133 for STC and the set value from the controller 101 to an address value, and outputs the data in the ROM 134 for GAIN/contrast at the designated address to a coordinate transforming circuit 135. The data outputted from the ROM 134 for GAIN/contrast is coordinate transformed by using the LUT 119 for coordinate transformation in the coordinate transforming circuit 135 and is interpolated by using the LUT 123 for interpolation in the interpolating circuit 122. The above-described operation is executed by the controller 101 at intervals with a predetermined period till the one rotation of the transducer 104.

FIG. 10 shows the operation setting unit 126 used for the above equipment. In the operation setting unit 126, values of the GAIN, STC, and contrast set at the using time are indicated by the number of lit-on LEDs constituting an indicator 141. The plurality of LEDs are arranged corresponding to a varied range of the set values.

For example, in the configuration in FIG. 8, the adjustment for GAIN, STC, and contrast must be implemented in a state in which image data is being received and transmitted (hereinafter, this state is referred to as a live state). Thus, in a state in which no image data is being received and transmitted (hereinafter, this state is referred to as a freeze state), data subjected to the adjustment for GAIN, STC, and contrast stored in the memory 120 is displayed on a screen and, therefore, there is a problem that the GAIN, STC, and contrast cannot be adjusted. The configuration in FIG. 9 necessitates the memory 132 for pre-process, ROM 133 for STC, and ROM 134 for GAIN/contrast to adjust the GAIN, STC, and contrast after freezing. There are problems that when handling an ultrasonic image composed of a plurality of frames, the memory 132 for pre-process needs a large capacity, and operation for reading ultrasonic data composed of any desired frames causes the adjustment of the memory 132 for pre-process by the controller 101 to become complicated.

If setting the GAIN, STC, and contrast at desired levels, the ROM 133 for STC and the ROM 134 for GAIN/contrast are exchanged and there is a problem that easy exchange is impossible.

As shown in FIG. 10, since the set values of the GAIN, STC, and contrast are indicated by the number of the lit-on LEDs constituting the indicator 141 in the operation setting unit 126, consumed current flowing to the operation setting unit 126 is increased. Therefore, design on a power source is necessary in view of the consumed power of the operation setting unit 126 on the equipment side and a problem to increase costs is caused.

The above and other objects, features and advantages of the invention will become more apparent from the following description when taken in conjunction with the accompanying drawings.

SUMMARY OF THE INVENTION

It is one object of the present invention to provide an ultrasonic diagnostic apparatus and an ultrasonic diagnostic method capable of adjusting gain and contrast with low costs both in the live state and in the freeze state.

It is another object of the present invention to provide an ultrasonic diagnostic apparatus capable of arbitrarily changing the setting of a dynamic range on software by changing table data.

It is further another object of the present invention to provide an ultrasonic diagnostic apparatus capable of adjusting the dynamic range of any desired frame with low costs by using a computer without providing a dedicated hardware.

According to the present invention, there is provided an ultrasonic diagnostic apparatus which comprises an echo signal adjust unit which can adjust gain or a dynamic range of an ultrasonic echo signal which is obtained by transmitting and receiving an ultrasonic wave to/from a body;

an input unit which inputs a parameter for adjusting the gain or dynamic range;

an image processing unit which processes the ultrasonic echo signal which is adjusted by the echo signal adjust unit, thereby obtaining ultrasonic image data;

a storing unit which stores the ultrasonic image data;

a calculating unit which reads the ultrasonic image data from the storing unit and performs a predetermined calculation of the ultrasonic image data; and an adjust unit which adjusts the echo signal adjust unit to adjust the gain or dynamic range based on the parameter inputted by the input unit when the parameter is inputted by the input unit during transmitting and receiving the ultrasonic wave and controls the calculating unit to read the ultrasonic image data from the storing unit for calculating the gain or dynamic range of the read ultrasonic image data based on the parameter inputted by the input unit when the parameter is inputted by the input unit during not transmitting and receiving the ultrasonic wave.

Other features and advantages of the present invention will appear more fully from the following description.

DESCRIPTION OF THE PREFERRED EMBODIMENTS (Configuration)

Figure 1:
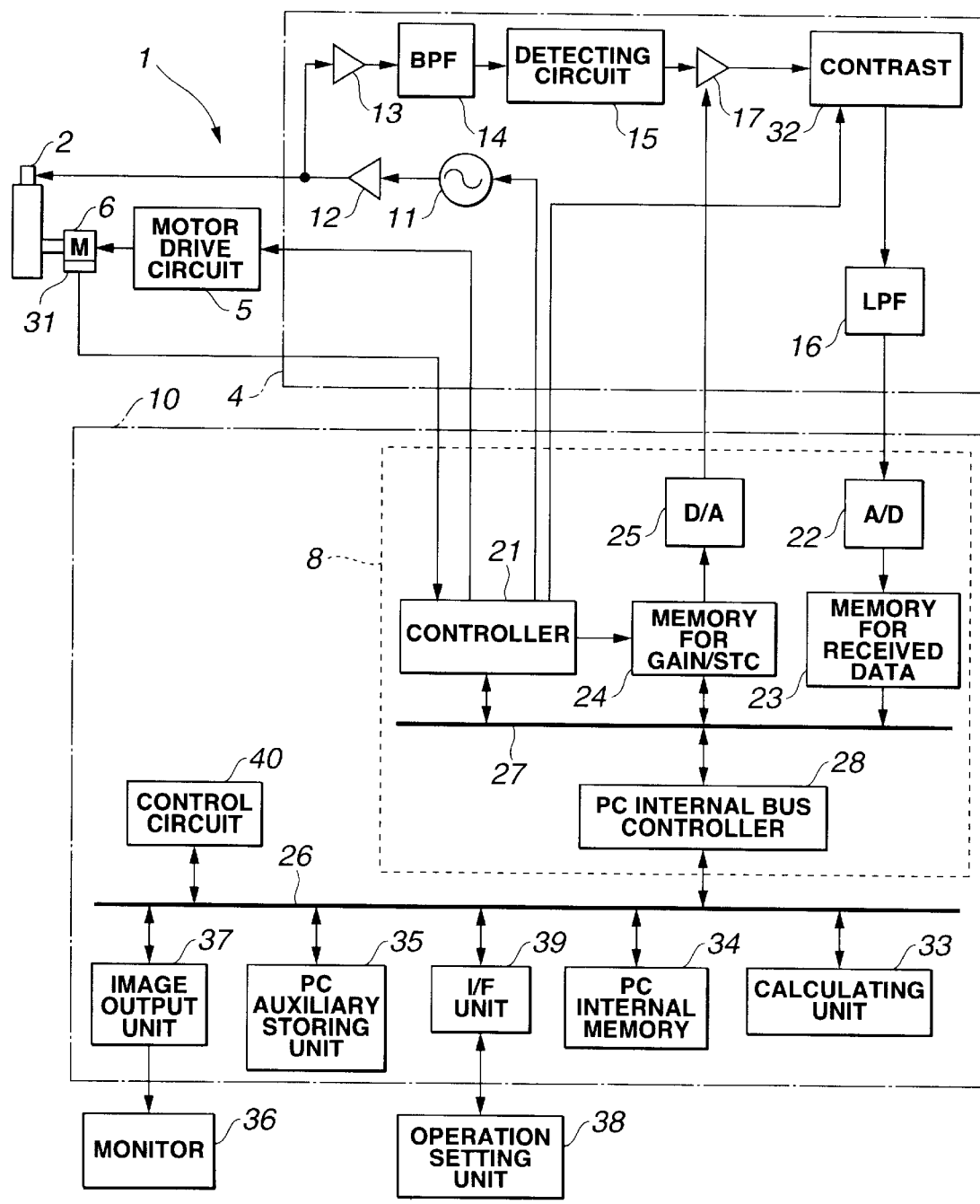
FIG. 1 is a diagram of the configuration of an ultrasonic diagnostic apparatus of a mechanical scanning system according to an embodiment of the present invention.

As shown in FIG. 1, according to an embodiment of the present invention, an ultrasonic diagnostic apparatus 1 of a mechanical scanning system comprises a transmitting and receiving unit 4 for transmitting and receiving an ultrasonic wave to/from an ultrasonic transducer 2 and a personal computer (hereinafter, referred to as PC) 10.

The PC 10 comprises a PC board 8, which is mounted detachably, for rotating the ultrasonic transducer 2 mounted on a rotary shaft of a motor 6 so as to become the center of the rotation by controlling a motor drive circuit 5 through the transmitting and receiving unit 4 and by rotating the motor 6 in response to a motor drive signal, and for subjecting an ultrasonic echo signal from the transmitting and receiving unit 4 to predetermined digital signal processing by controlling the transmitting and receiving unit 4, a PC internal memory 34 for storing a digital signal from the PC board 8, a calculating unit 33, and the like.

That is, the PC 10 controls the motor drive circuit 5, and the motor 6 rotates the ultrasonic transducer 2. As a result of the rotation of the ultrasonic transducer 2, the PC 10 captures a timing signal indicating a rotational position of the motor 6 which is outputted by a position detecting circuit 31 consisting of an encoder, etc. Based on the timing signal, the PC 10 controls a transmission signal generator 11 and a transmitting amplifier 12, and the ultrasonic transducer 2 connected to the transmitting amplifier 12 emits an ultrasonic pulse.

The transmitting and receiving unit 4 comprises the transmission signal generator 11 and the transmitting amplifier 12 for emitting the ultrasonic pulse in vivo from the ultrasonic transducer 2, a band-pass filter (BPF) 14 for receiving the ultrasonic echo signal of the ultrasonic pulse from the internal part of biological material by the ultrasonic transducer 2, amplifying the signal received by a receiving amplifier 13, and, thereafter, removing an unnecessary signal component from the amplified received signal, a detecting circuit 15 for detecting the received signal via the receiving amplifier 13 and BPF 14, and an amplifier 17 for GAIN/STC for amplifying the detection signal to a predetermined size and outputting the amplification signal to the PC board 8 in the PC 10 through a contrast circuit 32 and a low-pass filter (LPF) 16.

The PC board 8 in the PC 10 comprises a controller 21 for controlling the motor drive circuit 5 based on the timing signal, an A/D converter 22 for A/D converting the output of the amplifier 17 for GAIN/STC via the LPF 16 in the transmitting and receiving unit 4, a memory 23 for received data for storing a digital data converted by the A/D converter 22, a memory 24 for GAIN/STC for storing the amplification data from the amplifier 17 for GAIN/STC as digital data and outputting the signal synchronously with the timing signal of the controller 21, a D/A converter 25 for D/A converting an output of the memory 24 for GAIN/STC and changing the amplification amount of the amplifier 17 for GAIN/STC corresponding to the amplification of the analog signal by outputting the converted analog signal to the amplifier 17 for GAIN/STC, and a PC internal bus controller 28 for connecting a PC internal bus 26 to a local bus 27 in the PC board 8.

Connected to the PC internal bus 26, the calculating unit 33 for processing data in the PC 10, a PC internal memory 34 as a data storage area for the process by the calculating unit 33, a PC auxiliary storing unit 35 as a storage area of various data, an image output unit 37 for outputting an ultrasonic image obtained by the process of the calculating unit 33 to a monitor 36, an interface (I/F) unit 39 for transmitting and receiving data to/from an operation setting unit 38 for setting various data to the calculating unit 33, and a control circuit 40 for controlling each unit in the PC 10.

The PC auxiliary storing unit 35 may be, for example, not only a hard disk, but also a detachable unit from the PC 10 such as a compact flash card and it is not limited thereto.

(Operation)

To start with, operation of the live state will be described according to the present embodiment.

The controller 21 in the PC 10 controls the motor drive circuit 5 and drives the motor 6, thereby rotating the ultrasonic transducer 2. The rotation of the ultrasonic transducer 2 causes a sync signal outputted from the position detecting circuit 31 to be captured by the controller 21. The controller 21 controls the transmission signal generator 11 and the transmitting amplifier 12 synchronously with the sync signal. The ultrasonic transducer 2 connected to the transmitting amplifier 12 emits an ultrasonic pulse.

The ultrasonic transducer 2 receives an ultrasonic pulse echo from the biological material, and the receiving amplifier 13 amplifies the signal received by the ultrasonic transducer 2 to a predetermined size. The amplified received signal is detected by the detecting circuit 15 through the BPF 14, and is amplified to a predetermined size by the amplifier 17 for GAIN/STC based on a reference signal from the PC board 8, which will be described later. The received signal which is decreased as a distance is remoter is corrected to be increased as the time elapses.

The output signal of the amplifier 17 for GAIN/STC is converted into a predetermined contrast signal by the contrast circuit 32 based on the setting by the controller 21 in the PC board 8, which will be described later. The contrast signal passes through the LPF 16 and is outputted to the PC 10 from the transmitting and receiving unit 4. The received signal outputted by the receiving and receiving unit 4 is inputted to the PC board 8 mounted on the PC internal bus 26 in the PC 10.

The received signal inputted to the PC board 8 is converted into the digital signal by the A/D converter 22 and is stored in the memory 23 for received data. After storing data corresponding to one frame in the memory 23 for received data, this data corresponding to one frame passes through the memory 23 for received data and the PC internal bus controller 28 connected via the local bus 27 in the PC 8. The data is transferred to the PC internal memory 34 in the PC 10 via the PC internal bus 26.

The calculating unit 33 executes a program stored in the PC internal memory 34 and, thereby, the received data transferred to the PC internal memory 34 is subjected to the coordinate transformation and the interpolation. As a result, the calculating unit 33 generates the ultrasonic image data and stores the resultant data in the PC internal memory 34. An ultrasonic image is outputted to the monitor 36 via the image output unit 37.

If the operation setting unit 38 changes the GAIN and STC during the execution of the program in the calculating unit 33, the set values which are changed are converted into parameters for GAIN/STC, they pass through the PC internal bus 26 and the PC internal bus controller 28 in the PC board 8, and the parameter for GAIN/STC is set in the memory 24 for GAIN/STC. A control signal for GAIN/STC to be outputted by the DIA converter 25 is changed depending on the change of the contents of the memory 24 for GAIN/STC. Consequently, in the transmitting and receiving unit 4, gain of the amplifier 17 for GAIN/STC using the control signal for GAIN/STC is changed, and gain of the received signal is also changed.

In the change of contrast in the operation setting unit 38, similarly, the set value which is changed is converted into a contrast parameter, passes through the PC internal bus 26 and the PC internal bus controller 28 in the PC board 8, and is set in a register arranged in the controller 21. By changing the contents (parameter) of the register, the contrast circuit 31 in the transmitting and receiving circuit 4 is switched, thereby changing the contrast.

Figure 2:
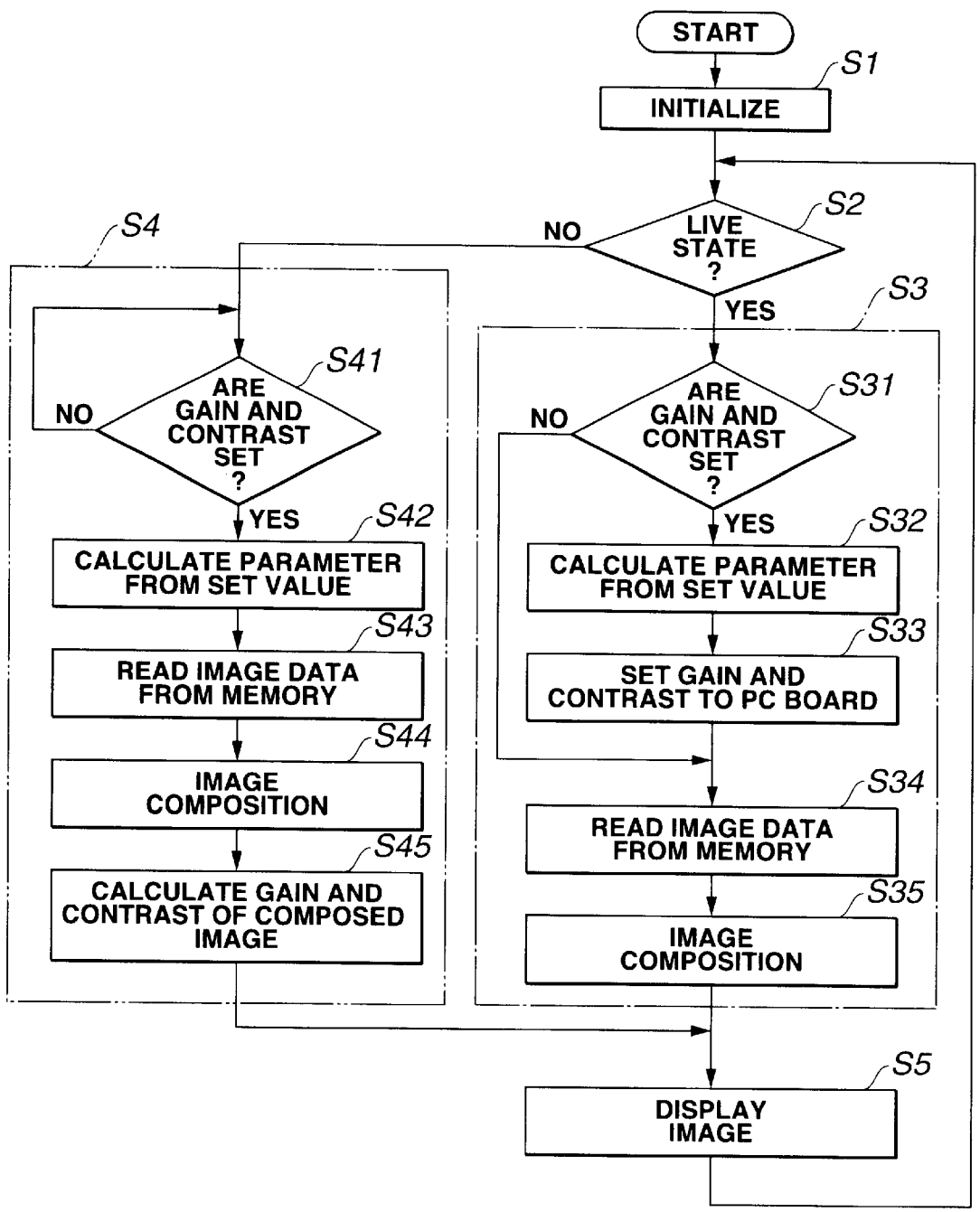
FIG. 2 is a flow chart for illustrating operation of the ultrasonic diagnostic apparatus of the mechanical scanning system in FIG. 1 according to the embodiment.

This series of operation indicates the live state. The freeze state is different from the live state. FIG. 2 shows a flow chart of a program process for gain and contrast in the live state and in the freeze state in the control circuit 40.

First, starting the program for gain and contrast which is stored in the PC internal memory 34, the control circuit 40 initializes the PC board 8 in step S1. The control circuit 40 determines whether operation of the components is in the live state or in the freeze state in step S2. If it is determined that the operation is in the live state, the processing routine shifts to step S31 in step S3 in the live state. It is determined that the operation is in the freeze state, the processing routine shifts to step S41 in step S4 in the freeze state.

The process in steps S31 to S35 in the live state is described below. The control circuit 40 determines which of the set values of GAIN, STC, and contrast is changed in step S31. If it is determined any one of the set values of GAIN, STC, and contrast is changed in step S31, the processing routine shifts to step S32. If it is determined that there is no change in setting, the processing routine shifts to step S34.

If it is determined that any one of the set values of GAIN, STC, and contrast is changed in step S31, the control circuit 40 converts any one of set values of GAIN, STC, and contrast, which is changed, into each parameter in step S32. The control circuit 40 stores the parameters of GAIN and STC in the memory 24 for GAIN/STC in the PC board 8, and stores the parameter of contrast in the register for contrast in the controller 21 in the PC board 8 in step S33. After that, the processing routine shifts to step S34.

The control circuit 40 reads the ultrasonic data stored in the PC internal memory 34 in step S34, and performs the coordinate transformation and the interpolation by using the calculating unit 33 in image composition in step S35. The control circuit 40 displays the ultrasonic image on the monitor 36 in step S5 and the processing routine returns to step S2 again.

The following shows the process in steps S41 to S45 when it is determined that the operation is in the freeze state in step S2. In step S41, the control circuit 40 determines which of the set values of GAIN, STC, and contrast is changed. If it is determined that any one of the set values of GAIN, STC, and contrast is changed in step 41, the processing routine shifts to step S42. If it is determined that there is no change in setting, the processing routine stops in step S41.

If it is determined that any one of the set values of GAIN, STC, and contrast is changed in step 41, the control circuit 40 converts any one of the set value of GAIN, STC, and contrast, which is changed, into each parameter in step S42.

The control circuit 40 reads the ultrasonic data stored in the PC internal memory 34 in step S43, and performs the coordinate transformation and the interpolation by using the calculating unit 33 in image composition in step S44. In step S45, the calculating unit 33 calculates the composite image based on the parameter of any one of the set values of GAIN, STC, and contrast which is generated in step S42. The control circuit 40 displays the ultrasonic image on the monitor 36 in step S5 and the processing routine returns to step S2 again.

As mentioned above, when the processing routine shifts to step S41 in the freeze state whereupon any one of the set values of GAIN, STC, and contrast is changed, the control circuit 40 converts the set values of GAIN and STC into parameters and sets them to the memory 24 for GAIN/STC on the PC board 8, and converts the set value of contrast into a parameter and set it to the controller 21 on the PC board 8 to reflect the set values even in the live state.

Figure 3:
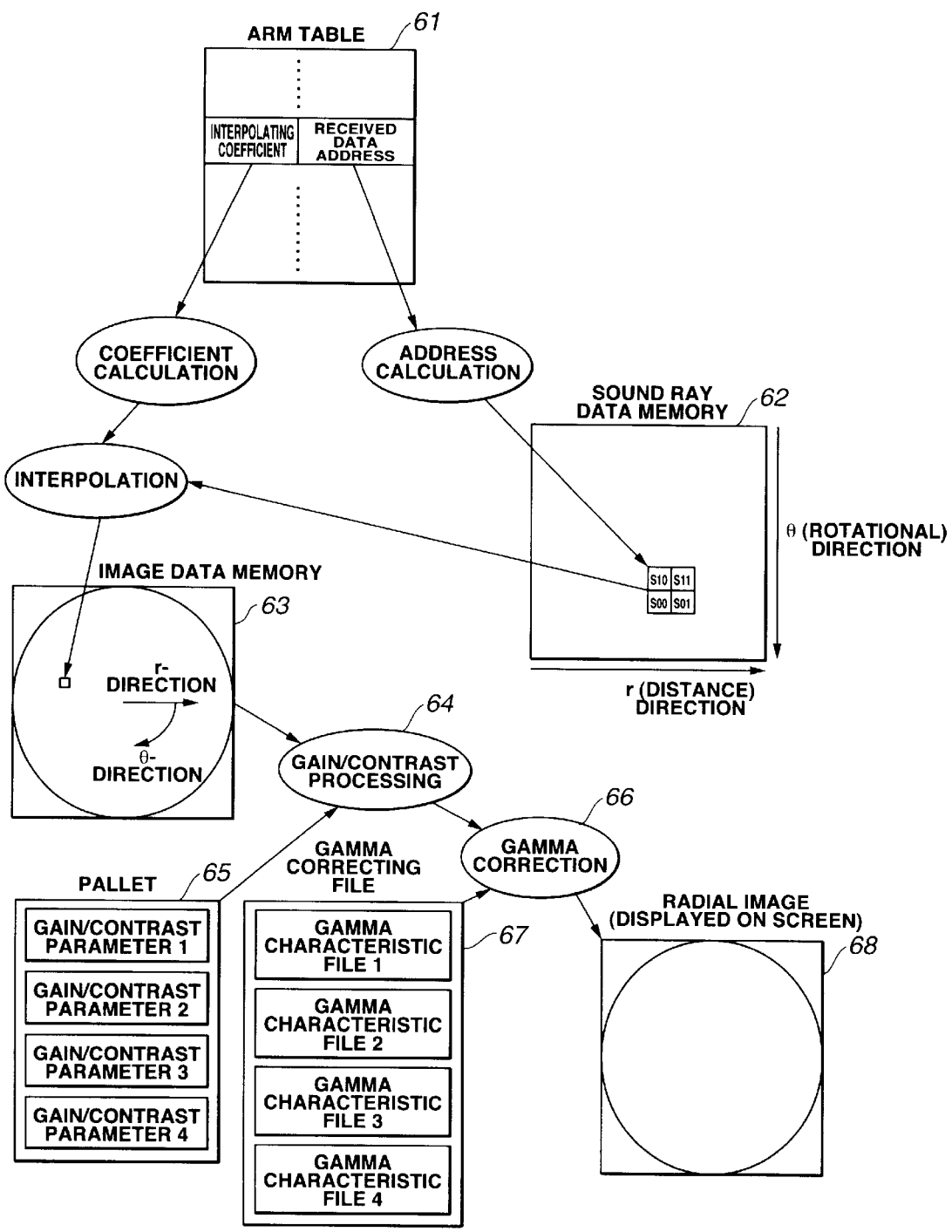
FIG. 3 is a first conceptual diagram showing the concept of gain and contrast processing on software in step S4 in a freeze state in the flow chart in FIG. 2 according to the embodiment.

FIG. 3 shows the concept of processes for gain and contrast on software in step S4 in the freeze state.

An ARM (Arbitrary Re-map Memory) table 61 stores therein an interpolating coefficient necessary for generating an arbitrary pixel and an address of a sound ray data memory 62 (set in the PC internal memory 34) in which the received data is stored.

Incidentally, the ARM table 61 exists in the PC internal memory 34 when the PC 10 is activated, and it exists in the PC auxiliary storing unit 35 when the PC 10 is not activated.

The sound ray data memory 62 stores therein the received data in an r (distance) direction corresponding to a propagation distance during transmission to reception of the ultrasonic wave and in a θ (angle) direction in which the ultrasonic transducer 2 rotates. The received data stored in the sound ray data memory 62 is subjected to the coordinate transformation and interpolation, thereby being radially stored in an image data memory 63 (set in the PC internal memory 34).

Here, for example, as disclosed in Japanese Patent Application No. 11-365367, first, the control circuit 40 reads an interpolating coefficient corresponding to a pixel P1 and an address of the sound ray data memory 62 from the ARM table 61 to obtain the pixel P1. Then, the control circuit 40 reads sound ray data from the sound ray data memory 62 by using this address, performs four-point interpolation by using both the read sound ray data and the interpolating coefficient read by the ARM table 61, and also performs the coordinate transformation, thereby obtaining the pixel P1.

The above-described process is based on the concept of the coordinate transformation, and is executed regardless of in the freeze state and in the live state.

The control circuit 40 carries out the process for gain and contrast in the freeze state based on the data stored in the image data memory 63.

The control circuit 40 stores in advance a setting table (hereinafter, referred to as a palette) 65 corresponding to set combinations of GAIN, STC, and contrast in the PC auxiliary storing unit 35 and the PC internal memory 34 in FIG. 1. If any one of the set values of the GAIN, STC, and contrast is changed, the control circuit 40 subjects the ultrasonic image data which is read by the image data memory 63 to a gain and contrast process 64 and a gamma characteristic calculation 66 by using the pallet 65 corresponding to the changed gain and contrast, thereby converting it into screen display data. The screen display data is displayed on the monitor 36 as a radial image 68.

Although the process for the GAIN, STC, and contrast is performed by using the pallet 65, it may be performed in the coordinate transformation. For example, the interpolating coefficient in the ARM table 61 is processed to obtain data including a gain adjust parameter of the GAIN and STC and a parameter of the contrast, and the sound ray data is read from the sound ray memory 62 by using the address which is read from the ARM table 61. The above-mentioned process for the GAIN, STC, and contrast may be performed in the interpolation using the sound ray data and interpolating coefficient.

Figure 4:
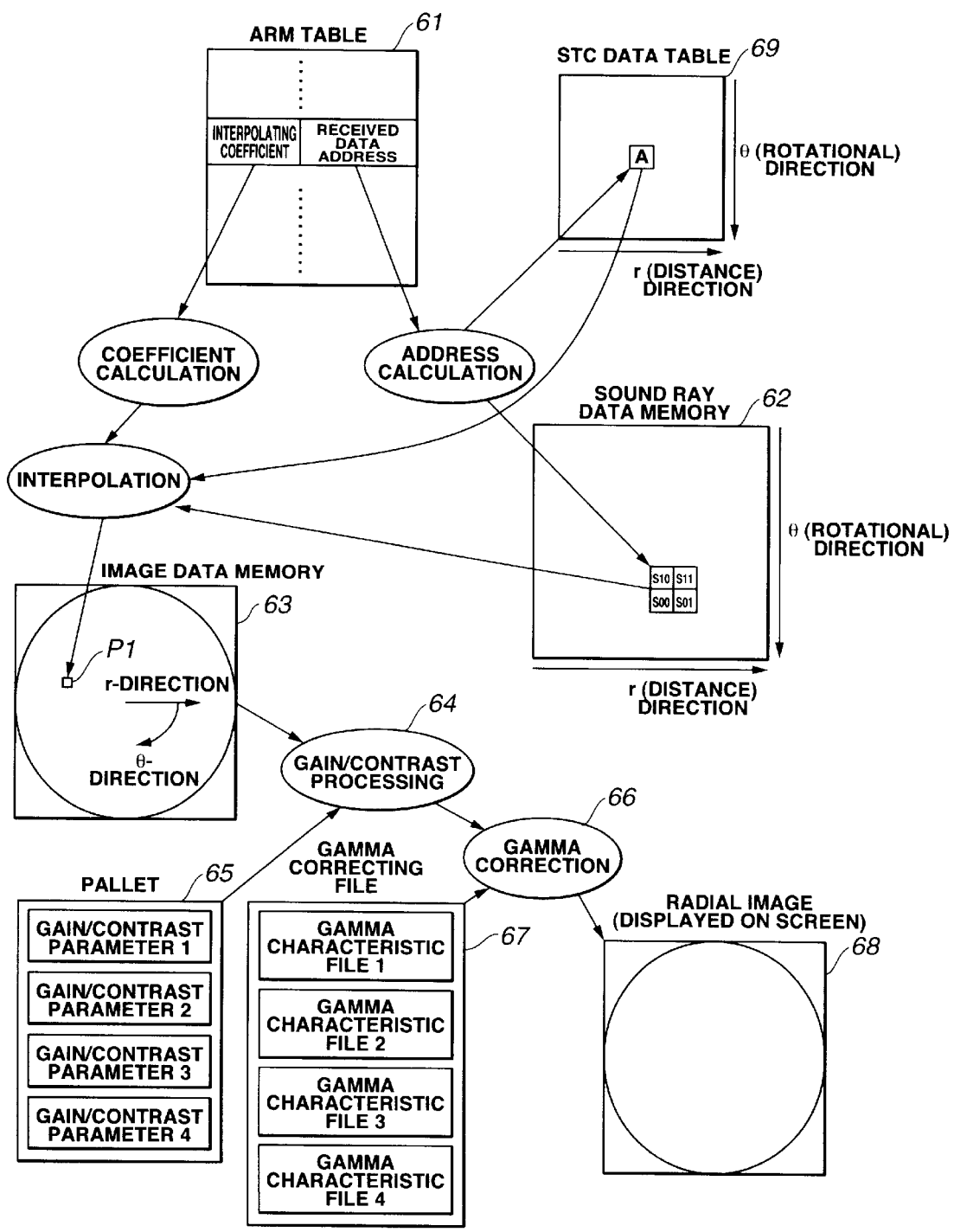
FIG. 4 is a second conceptual diagram showing the concept of gain and contrast processing on the software in step S4 in the freeze state in the flow chart in FIG. 2 according to the embodiment.

FIG. 4 shows a method for calculating only the STC in the coordinate transformation. An STC data table 69 stores therein a parameter of weighting the gain corresponding to a propagation distance during the transmission to the received of the ultrasonic wave similarly to the format stored in the sound ray data memory 62. The control circuit 40 reads an interpolating coefficient corresponding to the pixel P1 from the ARM table 61 and addresses of the sound ray data memory 62 and the STC data table 69 to obtain the pixel P1.

The control circuit 40 reads the sound ray data from the sound ray data memory 62 by using the addresses, reads a weighting parameter of the gain from the STC data table 69, and an interpolating coefficient is read from the ARM table 61. By using the sound ray, the weighting parameter of the gain, and the interpolating coefficient, the four-point interpolation, the coordinate transformation, and the weighting of gain are performed, thereby obtaining the pixel P1. Thereafter, the control circuit 40 uses the pallet corresponding to the setting of the GAIN and contrast in the gain/contrast process and executes the gamma characteristic process, thereby displaying the radial image on the screen.

Characteristics in the gamma correction to be applied are stored in the PC auxiliary storing unit 35 in FIG. 1 as a gamma characteristic file 67 serving as a file format. The ultrasonic image data read from the image data memory 63 is subjected to the gamma correction by using the selected gamma characteristic file 67, and may be displayed on the monitor 36 as the radial image 68.

The gamma correcting data used for the gamma correction may be based on a general-purpose file format to be outputted from general image processing application. This results in capturing gamma characteristics which are set by an image editing tool such as Photoshop, and gamma characteristics can be set to match with any desired setting of a user.

Although the above description embodies the software process in the freeze state, the gamma correction may be carried out in the live state as conversion from the image data memory 63 to the radial image 68.

Although the pallet 65 includes four gain/contrast parameters and the gamma characteristic file 67 includes four gamma characteristic files in FIGS. 3 and 4, the present invention is not limited thereto.

Figure 5:
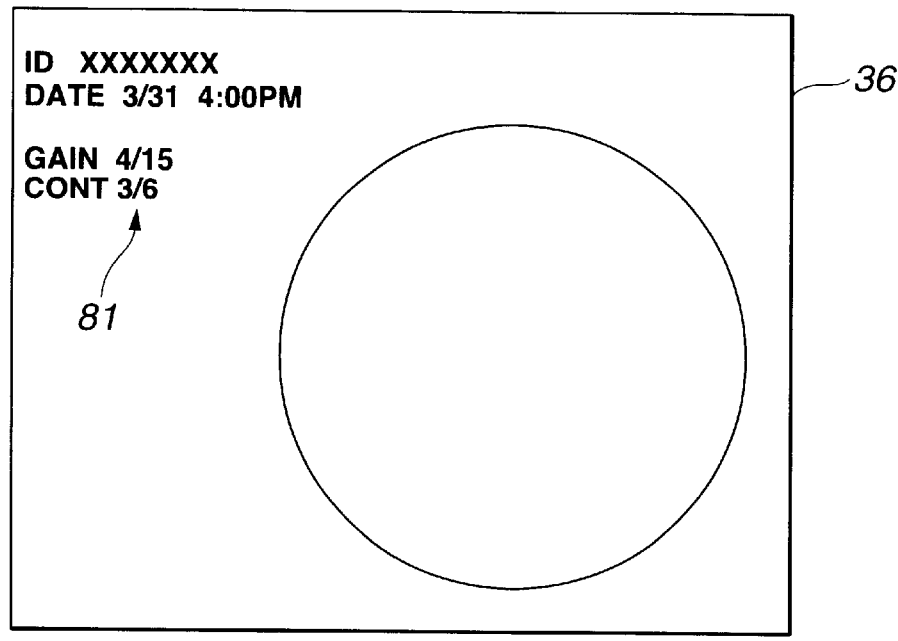
FIG. 5 is a diagram showing a first display example of set values of GAIN and STC as gain parameters and a set value of contrast on a monitor in FIG. 1 according to the embodiment.
Figure 6:
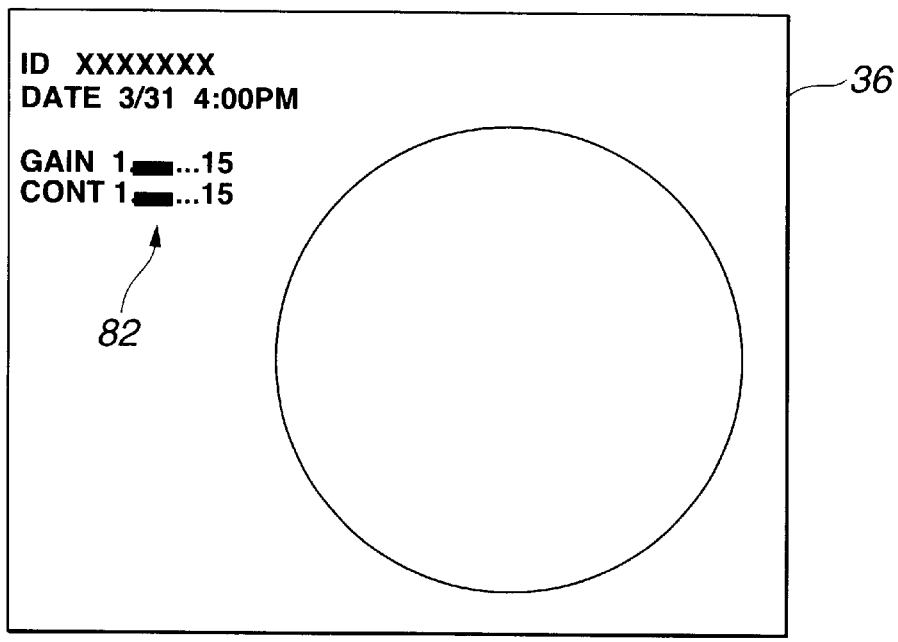
FIG. 6 is a diagram showing a second display example of the set values of the GAIN and STC as gain parameters and the set value of contrast on the monitor in FIG. 1 according to the embodiment.

The monitor 36 displays the set values of the GAIN as a gain parameter, STC and the contrast. FIGS. 5 and 6 show display examples of the set values on the monitor 36. FIG. 5 shows an example in which the set values and settable ranges of the GAIN and contrast are displayed by values (reference numeral 81). If there is a display space on the screen, the set values and settable range of the GAIN, STC and contrast may be graphically indicated by a line and a dotted line, respectively, (reference numeral 82) as shown in FIG. 6.

As shown in FIGS. 5 and 6, the set values and settable range of the GAIN, STC and contrast are displayed on the monitor 36. Consequently, the operation setting unit 38 does not need the above display.

Figure 7:
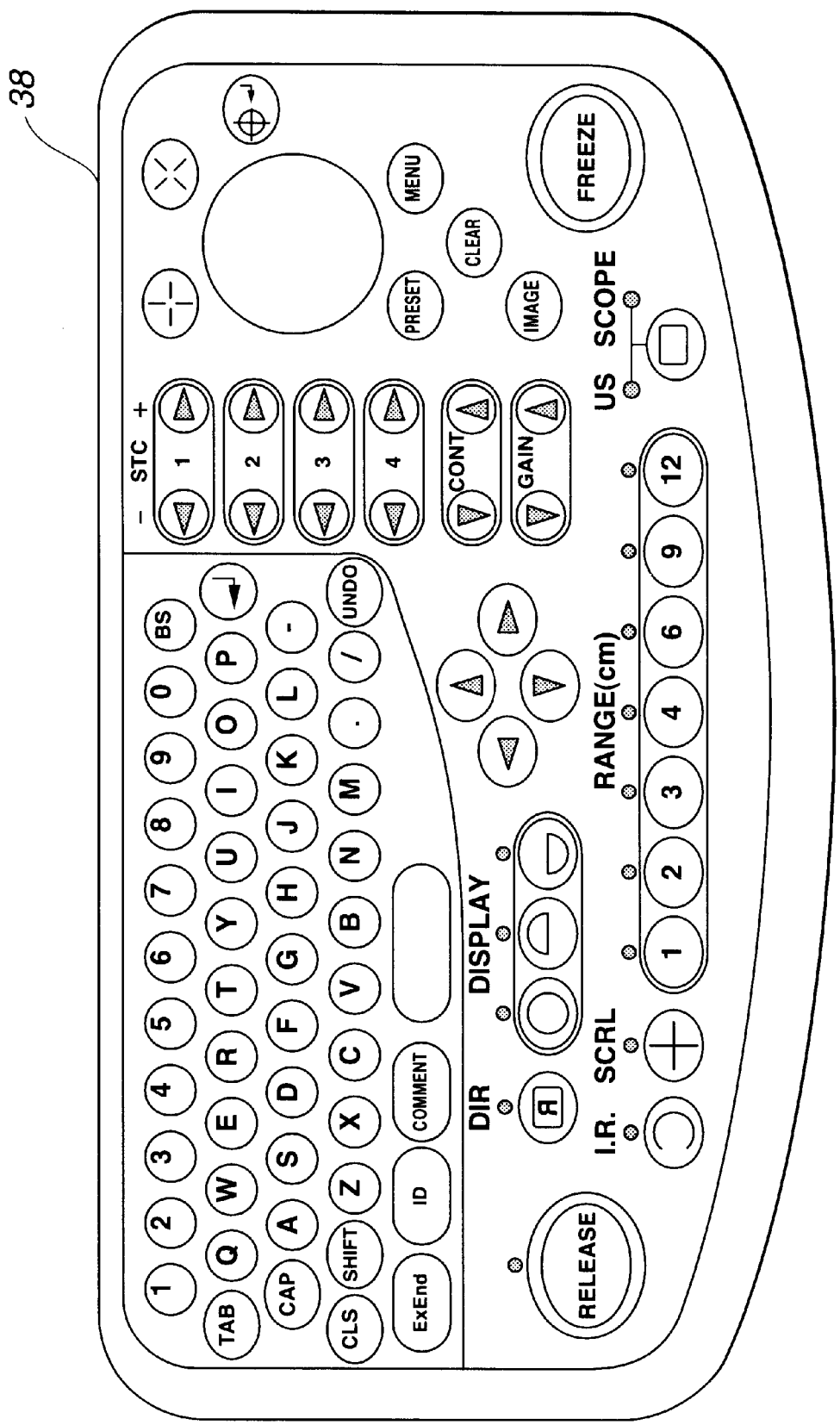
FIG. 7 is a diagram showing the external appearance of an operation setting unit in FIG. 1 according to the embodiment.
Figure 8:
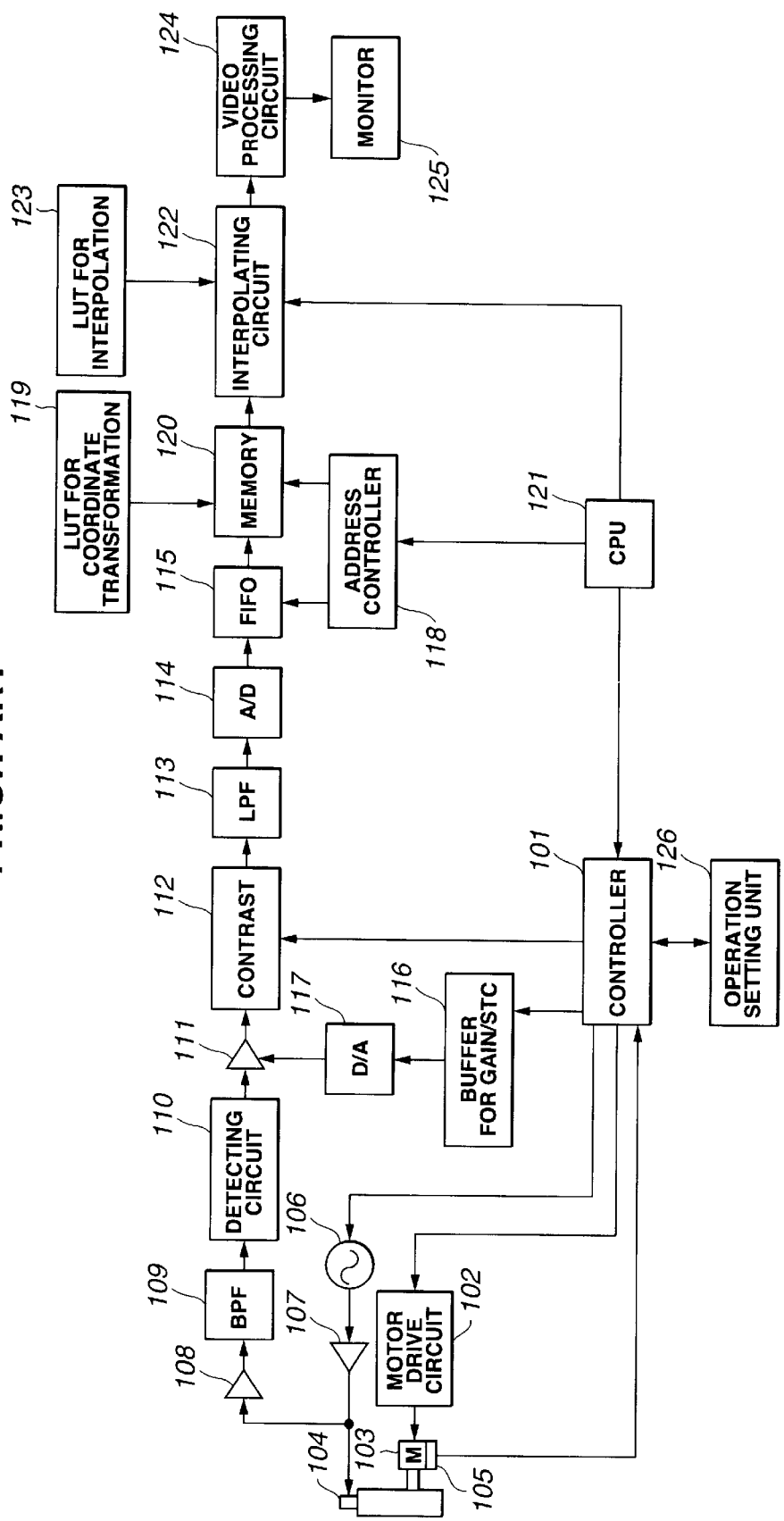
FIG. 8 is a diagram showing a first example of the configuration of a conventional ultrasonic diagnostic apparatus of a mechanical scanning system.
Figure 9:
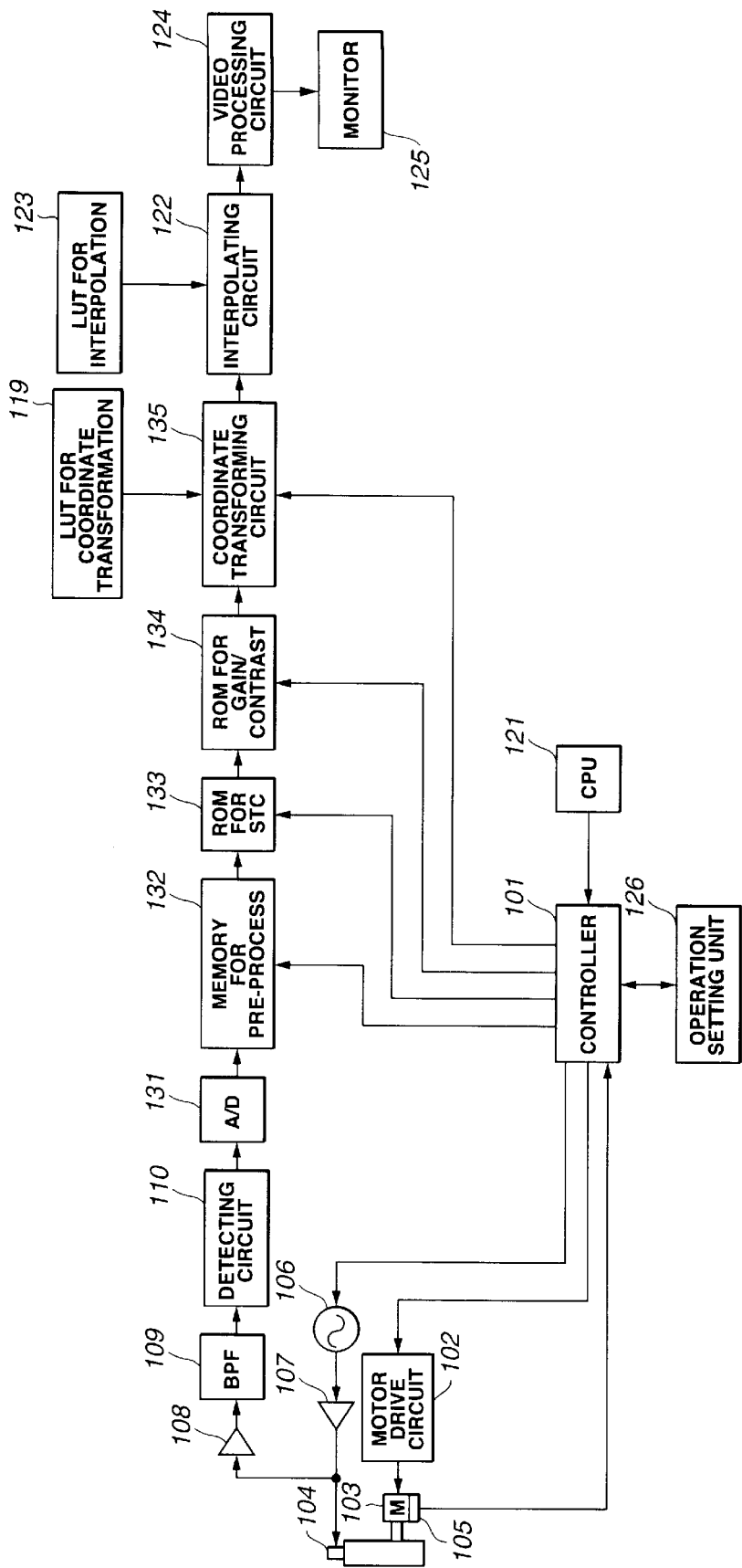
FIG. 9 is a block diagram showing a second example of the configuration of the conventional ultrasonic diagnostic apparatus of the mechanical scanning system.
Figure 10:
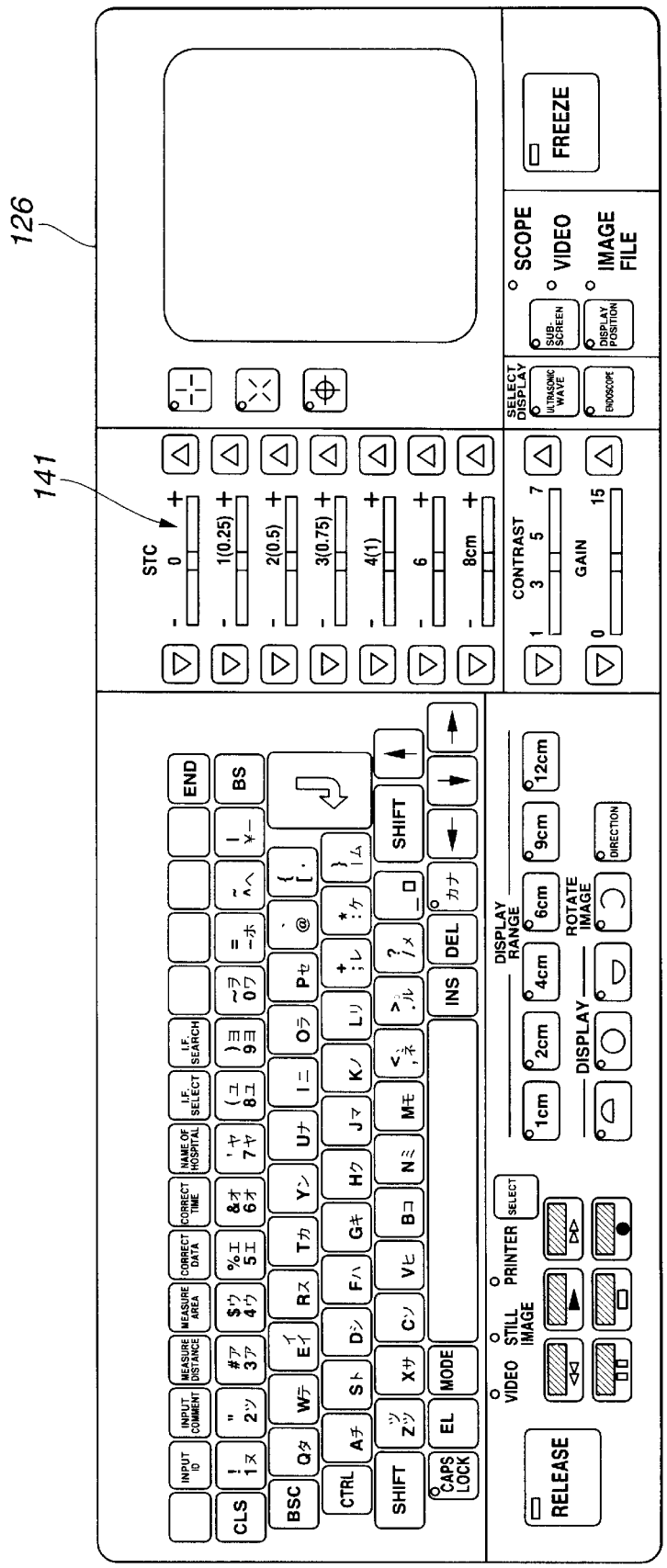
FIG. 10 is a diagram showing the external appearance of a conventional operation setting unit.

FIG. 7 shows an example of the operation setting unit 38 according to the present embodiment. In the operation setting unit 38 shown in FIG. 7, only symbols indicating the increase in set values and phenomena are used for the GAIN, STC, and contrast. The operation setting unit 38 necessitates no plural LEDs indicating the settable range like a conventional indicator.

(Advantages)

According to the present invention, the gain adjust for GAIN and STC and the contrast adjust are executed based on the calculation of the calculating unit 33 by using the ultrasonic data which is stored in the memory in the PC 10 both in the live state and in freeze state. Thereby, a large capacity memory for storing the ultrasonic data comprising a plurality of frames is unnecessary and, therefore, the ultrasonic diagnostic apparatus of the mechanical scanning system can be obtained with low costs.

The PC auxiliary storing unit 35 in the PC 10 can be exchanged, to thereby provide the ultrasonic diagnostic apparatus of the mechanical scanning system in which a dynamic range can be easily changed to match with any desired setting of the user.

Further, the monitor 36 displays the set values and the settable range of the GAIN and contrast on the screen on which the ultrasonic image is displayed. Thereby, another circuit or means for displaying the settable range does not need to be provided for the operation setting unit 38, etc. Therefore, the ultrasonic diagnostic apparatus of the mechanical scanning system can be provided with low costs.

Having described the preferred embodiments of the invention referring to the accompanying drawings, it is to be understood that the invention is not limited to those precise embodiments and that various changes and modifications thereof could be effected by one skilled in the art without departing from the spirit or scope of the invention as defined in the appended claims.

What is claimed is:

1. An ultrasonic diagnostic apparatus comprising:
an echo signal adjust unit which can adjust gain or a dynamic range of an ultrasonic echo signal which is obtained by transmitting and receiving an ultrasonic wave to/from a body;
an input unit which inputs a parameter for adjusting the gain or dynamic range;
an image processing unit which processes the ultrasonic echo signal which is adjusted by the echo signal adjust unit, thereby obtaining ultrasonic image data;
a storing unit which stores the ultrasonic image data;
a calculating unit which reads the ultrasonic image data from the storing unit and performs a predetermined calculation of the ultrasonic image data; and
an adjust unit which adjusts the echo signal adjust unit to adjust the gain or dynamic range based on the parameter inputted by the input unit when the parameter is inputted by the input unit during transmitting and receiving the ultrasonic wave and controls the calculating unit to read the ultrasonic image data from the storing unit for calculating the gain or dynamic range of the read ultrasonic image data based on the parameter inputted by the input unit when the parameter is inputted by the input unit during not transmitting and receiving the ultrasonic wave.

2. An ultrasonic diagnostic apparatus according to claim 1, further comprising:
a set value input unit which inputs set values for setting the gain and the dynamic range of the ultrasonic image data; and
a display control unit which displays the set values of the gain and the dynamic range on a screen of a monitor and also displays a settable range of the gain and dynamic range.

3. An ultrasonic diagnostic method comprising:
an echo signal adjust step of adjusting gain or a dynamic range of an ultrasonic echo signal which is obtained by transmitting and receiving an ultrasonic wave to/from a body;
an input step of inputting a parameter for adjusting the gain or dynamic range;
an image processing step of processing the ultrasonic echo signal which is adjusted in the echo signal adjust step, thereby obtaining ultrasonic image data;
a storing step of storing the ultrasonic image data;
a calculating step of reading the ultrasonic image data which is stored in the storing step for performing a predetermined calculation of the ultrasonic image data; and
a process selecting step of, when the parameter is inputted during transmitting and receiving the ultrasonic wave, selecting the echo signal adjust step to adjust the gain or dynamic range in the echo signal adjust step based on the inputted parameter and, when the parameter is inputted during not transmitting and receiving the ultrasonic wave, selecting the calculating step to read the ultrasonic image data for calculating the gain or dynamic range of the read ultrasonic image data in the calculating step based on the inputted parameter.

4. An ultrasonic diagnostic apparatus comprising:
a PC board which converts an ultrasonic echo signal obtained by an ultrasonic transmitting and receiving unit for transmitting and receiving an ultrasonic wave to/from a body into digital data, and outputs an amplitude adjust signal for adjusting an amplitude of the ultrasonic echo signal to the ultrasonic transmitting and receiving unit;
a storing unit which receives the digital data converted by the PC board and stores a program for calculating gain of the received digital data; and
a calculating unit which executes the program for generating an ultrasonic image from the digital data.

5. An ultrasonic diagnostic apparatus according to claim 4, wherein
the storing unit can be exchanged.

6. An ultrasonic diagnostic apparatus according to claim 4, wherein
the program for calculating the gain allows the received digital data to be stored in the storing unit as received data per frame, reads the received data corresponding to a predetermined frame from the received data stored in the storing unit, and calculates the gain of the read received data.

* * * * *